(12) United States Patent
Seo et al.

(10) Patent No.: US 10,760,184 B2
(45) Date of Patent: Sep. 1, 2020

(54) PREPARATION METHOD OF SUPERABSORBENT POLYMER FIBER

(71) Applicant: LG Chem, Ltd., Seoul (KR)

(72) Inventors: Jin Seok Seo, Daejeon (KR); Young Sam Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/766,599

(22) PCT Filed: Jan. 9, 2017

(86) PCT No.: PCT/KR2017/000282
§ 371 (c)(1),
(2) Date: Apr. 6, 2018

(87) PCT Pub. No.: WO2017/164496
PCT Pub. Date: Sep. 28, 2017

(65) Prior Publication Data
US 2018/0313000 A1    Nov. 1, 2018

(30) Foreign Application Priority Data

Mar. 24, 2016  (KR) .......................... 10-2016-0035407

(51) Int. Cl.
*D01F 6/16* (2006.01)
*D04H 13/00* (2006.01)
(Continued)

(52) U.S. Cl.
CPC .............. *D01F 6/16* (2013.01); *A61L 15/24* (2013.01); *A61L 15/42* (2013.01); *A61L 15/60* (2013.01);
(Continued)

(58) Field of Classification Search
None
See application file for complete search history.

(56) References Cited

U.S. PATENT DOCUMENTS 3,731,411 A * 5/1973 Barber ................ D06M 15/263
                                                            38/144
4,399,255 A * 8/1983 Smith .................... A61L 15/225
                                                            106/166.51
(Continued)

FOREIGN PATENT DOCUMENTS

CN           1051510 A      5/1991
CN           1234809 A      11/1999
(Continued)

OTHER PUBLICATIONS

Extended European Search Report including Written Opinion for Application No. EP17770467.3 dated Aug. 6, 2018.
(Continued)

*Primary Examiner* — Randy P Gulakowski
*Assistant Examiner* — Ha S Nguyen
(74) *Attorney, Agent, or Firm* — Lerner, David, Littenberg, Krumholz & Mentlik, LLP

(57) ABSTRACT

The present invention relates to a method for preparing superabsorbent polymer fiber and superabsorbent polymer fiber prepared thereby. According to the preparation method of the present invention, superabsorbent polymer in the form of fiber or non-woven fabric that maintains super absorbency function can be prepared.

14 Claims, 1 Drawing Sheet

(51) Int. Cl.
*A61L 15/24* (2006.01)
*A61L 15/42* (2006.01)
*A61L 15/60* (2006.01)
*D01F 1/02* (2006.01)
*C08F 20/06* (2006.01)
*D04H 1/42* (2012.01)
*C08L 33/02* (2006.01)
*D01D 1/02* (2006.01)
*D01D 5/18* (2006.01)
*D01D 10/06* (2006.01)

(52) U.S. Cl.
CPC .............. *C08F 20/06* (2013.01); *C08L 33/02* (2013.01); *D01D 1/02* (2013.01); *D01D 5/18* (2013.01); *D01D 10/06* (2013.01); *D01F 1/02* (2013.01); *D04H 1/42* (2013.01); *D04H 13/00* (2013.01); *C08L 2203/02* (2013.01); *C08L 2205/16* (2013.01); *D10B 2321/08* (2013.01); *D10B 2401/022* (2013.01)

(56) References Cited

U.S. PATENT DOCUMENTS

| | | | |
|---|---|---|---|
| 5,079,306 | A | 1/1992 | Le-Khac |
| 5,856,410 | A | 1/1999 | Carrico et al. |
| 6,503,979 | B1 | 1/2003 | Funk et al. |
| 2003/0125684 | A1 | 7/2003 | Qin |
| 2003/0219594 | A1 | 11/2003 | Qin et al. |
| 2004/0142113 | A1 | 7/2004 | Anderson et al. |
| 2005/0245393 | A1 | 11/2005 | Herfert et al. |
| 2006/0057375 | A1 | 3/2006 | Harren et al. |
| 2008/0081189 | A1* | 4/2008 | Weerawarna ........... A61L 15/60 428/364 |
| 2008/0081190 | A1 | 4/2008 | Weerawarna et al. |
| 2008/0119626 | A1 | 5/2008 | Fujimaru et al. |
| 2013/0146810 | A1 | 6/2013 | Zhang et al. |
| 2014/0091033 | A1 | 4/2014 | Kitano |
| 2015/0211149 | A1* | 7/2015 | Lamanac ................. D01D 5/18 264/8 |
| 2016/0047061 | A1 | 2/2016 | Huang et al. |
| 2016/0069000 | A1 | 3/2016 | Kay et al. |
| 2016/0280862 | A1 | 9/2016 | Kim et al. |
| 2017/0306528 | A1 | 10/2017 | Seo et al. |

FOREIGN PATENT DOCUMENTS

| | | | |
|---|---|---|---|
| CN | 101161881 | A | 4/2008 |
| CN | 102161725 | A | 8/2011 |
| CN | 103160952 | A * | 6/2013 |
| CN | 103254335 | A | 8/2013 |
| CN | 104356281 | A | 2/2015 |
| CN | 103160952 | B | 4/2015 |
| CN | 105113039 | A * | 12/2015 |
| EP | 0268498 | B1 | 10/1992 |
| EP | 3190216 | A1 | 7/2017 |
| JP | 63028912 | A * | 2/1988 |
| JP | 01103643 | A * | 4/1989 |
| JP | H06080818 | A | 3/1994 |
| JP | H06136071 | A | 5/1994 |
| JP | 2008537553 | A | 9/2008 |
| JP | 2015178608 | A | 10/2015 |
| KR | 20050008710 | A | 1/2005 |
| KR | 20050025333 | A | 3/2005 |
| KR | 20050036975 | A | 4/2005 |
| KR | 20070119040 | A | 12/2007 |
| KR | 20080030939 | A | 4/2008 |
| KR | 20140017680 | A | 2/2014 |
| KR | 20140105583 | A | 9/2014 |
| KR | 20150146396 | A | 12/2015 |
| WO | 1994004724 | A1 | 3/1994 |
| WO | 2013083698 | A1 | 6/2013 |
| WO | 2015015331 | A1 | 2/2015 |

OTHER PUBLICATIONS

Lenka Martinova et al: "Nanofiber Sheets with the Superabsorbent Properties", Advanced Materials Research, vol. 354-355, Jan. 1, 2011, pp. 210-215, XP008161216.
International Search Report for Application No. PCT/KR2017/000282 dated Apr. 28, 2017.
Schwalm, Reinhold, "UV Coatings: Basics, Recent Developments and New Applications", Elsevier Science, Dec. 21, 2016, p. 115.
Odian, George, "Principles of Polymerization", John Wiley and Sons, Inc. Oct. 1981, p. 203.
Cash, David, "Superabsorbent Polymers (SAP)", Chem News, May 2007.
Chinese Search Report for Application No. 201780003620.2, dated Dec. 4, 2019, pp. 1-3.
Sarkar K, Gomez C, Zambrano S, Ramirez M, de Hoyos E, Vasquez H, Lozano K. Electrospinning to forcespinning™. Materials today. Nov. 1, 2010;13(11):12-4.
Buchholz, F. L., & Graham, A. T. (1998). Modern superabsorbent polymer technology. John! Wiley & Sons, Inc, 605 Third Ave, New York, NY 10016, USA, 1998. 279.
Third Party Observation for EP17770467.3 dated Jun. 17, 2020; 12 pages.

* cited by examiner

PREPARATION METHOD OF SUPERABSORBENT POLYMER FIBER

CROSS-REFERENCE TO RELATED APPLICATION(S)

The present application is a national phase entry under 35 U.S.C. § 371 of International Application No. PCT/KR2017/000282, filed on Jan. 9, 2017,which claims the benefit of Korean Patent Application No. 10-2016-0035407, filed on Mar. 24, 2016 with the Korean Intellectual Property Office, the disclosures of which are herein incorporated by reference.

BACKGROUND OF INVENTION (a) Field of the Invention

The present invention relates to a method for preparing superabsorbent polymer fiber.

(b) Description of the Related Art

Super absorbent polymer (SAP) is synthetic polymer material that can absorb moisture of 500 to 1000 times of self-weight, and began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, fomentation material, etc. Thus, superabsorbent polymer known to have superior absorption capacity compared to the existing absorption materials has high market value because the application range is increasingly widening.

Currently, superabsorbent polymer is prepared and used in the form of powder. Such superabsorbent polymer in the form of powder may be scattered or leaked when it is used to prepare hygienic goods or practically used, and the range of use is limited because it should be used together with a substrate of a specific form. And, the preparation process of superabsorbent polymer powder is complicated and involves many factors to be controlled.

SUMMARY OF THE INVENTION

In order to solve the problems of the prior art, it is an object of the present invention to provide a preparation method capable of efficiently preparing superabsorbent polymer in a novel form, i.e., in the form of fiber or non-woven fabric, while maintaining super absorbency function, and superabsorbent polymer fiber prepared thereby.

In order to achieve the object, the present invention provides a method for preparing superabsorbent polymer fiber comprising the steps of:

polymerizing water-soluble ethylenically unsaturated monomers and a crosslinking agent and preparing a polymer aqueous solution comprising polymer wherein the polymerization of the water-soluble ethylenically unsaturated monomers and crosslinking agent are crosslinked;

adding sodium hydroxide to the polymer aqueous solution to prepare a neutralized spinning solution; and centrifugally spinning the spinning solution, and then, drying.

And, the present invention provides superabsorbent polymer fiber obtained by the above preparation method.

According to the preparation method of superabsorbent polymer fiber, the process can be minimized because superabsorbent polymer is prepared in the form of fiber or non-woven fabric. And, by using centrifugal spinning, the construction of equipment is relatively simple, energy consumption is low, and there is a small limitation in the kind of polymer that can be spun.

And, since it has the form of fiber while maintaining super absorbency function of absorbing much more amount of moisture than its own weight, unlike powder superabsorbent polymer, there is no concern of scattering or leakage when applied for a product.

Since the superabsorbent polymer fiber according to the preparation method of the present invention has a form of fiber unlike superabsorbent polymer commonly obtained in the form of powder, it can be productized in the form of non-woven fabric, and it can be easily applied for pulpless products.

And, since it can be directly spun on a substrate during the preparation, process steps and required facilities can be simplified.

Moreover, since it has fiber-like properties and exhibits flexibility and processibility, it can be modified into various shapes and can be applied more widely, and thus, it is highly likely to be developed as next generation superabsorbent polymer products having novel forms and uses.

DETAILED DESCRIPTION OF THE EMBODIMENTS

Figure 1:
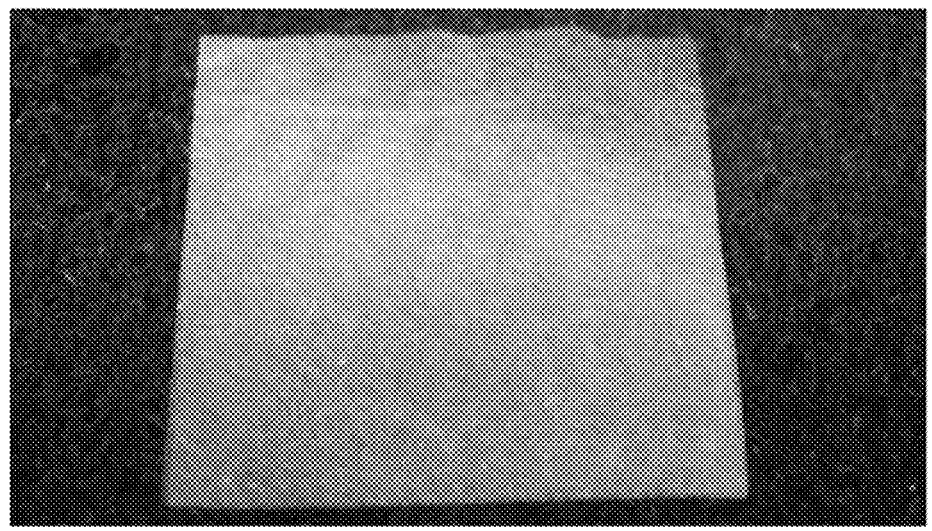
FIG. 1 is the photograph of the superabsorbent polymer fiber according to example of the present invention.

Technical terms in the present specification are only for mentioning specific embodiments, and they are not intended to restrict the present invention unless there is a particular mention about them. The singular expressions used herein may include the plural expressions unless they are differently expressed contextually. The meaning of the term "include" used in the specification embodies specific characteristics, areas, essences, steps, actions, elements, and/or components, and does not exclude existence or addition of other specific characteristics, areas, essences, steps, actions, elements, components, and/or groups.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, a method for preparing superabsorbent polymer fiber according to specific embodiment of the present invention will be explained in more detail.

According to one embodiment of the present invention, a method for preparing superabsorbent polymer fiber comprising the steps of: polymerizing water-soluble ethylenically unsaturated monomers and a crosslinking agent to prepare a polymer aqueous solution comprising polymer wherein the water-soluble ethylenically unsaturated monomers and crosslinking agent are polymerized; adding sodium hydroxide to the polymer aqueous solution to prepare a neutralized spinning solution; and centrifugally spinning the spinning solution, and then, drying, is provided.

In the preparation method of superabsorbent polymer fiber according to the present invention, first, water-soluble ethylenically unsaturated monomers and a crosslinking agent are polymerized to prepare a polymer aqueous solution comprising polymer wherein the water-soluble ethylenically unsaturated monomers and crosslinking agent are polymerized.

In the preparation method of superabsorbent polymer fiber according to the present invention, as the water-soluble ethylenically unsaturated monomers, monomers commonly used in the preparation of superabsorbent polymer may be used without limitation in the constructions, but preferably, one or more selected from the group consisting of anionic monomers and salts thereof, non-ionic hydrophilic containing monomers, and amino group containing unsaturated monomers and quarternarization products thereof may be used.

Specifically, as the water-soluble ethylenically unsaturated monomers, one or more selected from the group consisting of anionic monomers and salts thereof such as isobutylene, acrylic acid, polyacrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid or 2-(meth)acrylamide-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth)acrylate, methylacrylate, hydroxylpropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternarized products thereof, may be preferably used.

And, one or more selected from the group consisting of isobutylene, maleic anhydride, polyacrylic acid, acrylic acid, methylacrylate, hydroxypropyl (meth)acrylate may be more preferable.

Most preferably, acrylic acid or salts thereof may be used, and by using such monomers, superabsorbent polymer with improved absorption property can be obtained.

The crosslinking agent that is polymerized with the water-soluble ethylenically unsaturated monomers to form polymer is not limited in terms of its construction as long as it is a compound capable of reacting with the functional group of the monomers, but in order to improve the properties of produced superabsorbent polymer fiber, one or more selected from the group consisting of polyhydric alcohol compounds; (meth)acrylate-based compounds; hydroxyl alkyl (meth)acrylate-based compounds; epoxy compounds; polyamine compounds; haloepoxy compounds; condensation products of haloepoxy compounds; oxazoline compounds; mono-, di- or polyoxazolidinone compounds; cyclic urea compounds; multivalent metal salts; and alkylene carbonate compounds may be used.

Specifically, as the polyhydric alcohol compound, one or more selected from the group consisting of mono-, di-, tri-, tetra- or polyethyleneglycol, monopropyleneglycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexanedimethanol may be used.

And, as the (meth)acrylate-based compound, poly(ethyleneglycol)diacrylate may be used.

And, as the epoxy compound, ethylene glycol diglycidyl ether, glycidol, etc. may be used, and as the polyamine compound, one or more selected from the group consisting of ethylenediamine, diethylenetriamine, triethylenetetramine, tetraethylenepentamine, pentaethylenehexamine, polyethyleneimine and polyamide polyamine may be used.

And, as the haloepoxy compound, epichlorohydrin, epibromohydrin and α-methylepichlorohydrin may be used. And, as the mono-, di- or polyoxazolidinone compound, 2-oxazolidinone, etc. may be used. And, as the alkylene carbonate compound, ethylene carbonate, etc. may be used. There compounds may be used alone or in combinations with each other. Meanwhile, in order to increase the efficiency of the crosslinking process, it is preferable that the crosslinking agent comprises one or more polyhydric alcohol compounds, and more preferably, C2-10 polyhydric alcohol compounds may be used.

As the crosslinking agent, preferably, a hydroxyl alkyl (meth)acrylate-based compound having a functional group capable of reacting with the functional group of the monomers on one side, and simultaneously having a functional group that can be crosslinked with each other on the other side may be used. As such, when the hydroxyl alkyl (meth)acrylate-based compound is used as a crosslinking agent, in the step of centrifugal spinning and drying as described below, the crosslinking reaction of polymer may additionally occur, thereby forming a network structure.

As the hydroxyl alkyl (meth)acrylate-based compound, hydroxyl ethyl acrylate, hydroxyl ethyl methacrylate, etc. may be used.

Although the content of the crosslinking agent may be appropriately selected according to the kind of the crosslinking agent added or reaction conditions, in order to induce a proper crosslinking reaction, it may be included such that the mole ratio of the water-soluble ethylenically unsaturated monomers and crosslinking agent becomes about 95:5 to about 99.9:0.1, or about 97:3 to about 99.9:0.1, or about 98:2 to about 99.9:0.1.

The polymer aqueous solution comprises polymer prepared as a high molecular compound by the polymerization of the above explained water-soluble ethylenically unsaturated monomers and crosslinking agent. Here, the polymer means to include a high molecular compound prepared by the copolymerization of two or more kinds of monomers, as well as a high molecular compound prepared by the polymerization of one kind of monomers.

The weight average molecular weight of the polymer wherein the water-soluble ethylenically unsaturated monomers and crosslinking agent are polymerized is not specifically limited, but may be in the range of about 500,000 to about 1,200,000 g/mol.

According to one embodiment of the present invention, a polymer aqueous solution comprising polymer wherein the water-soluble ethylenically unsaturated monomers and crosslinking agent are polymerized together may be obtained by dissolving the water-soluble ethylenically unsaturated monomers, the crosslinking agent and a polymerization initiator in water to form a monomer composition of an aqueous solution state, and progressing thermal polymerization or photopolymerization of the monomer composition.

Here, the polymerization initiator used during the polymerization is not specifically limited as long as it is commonly used for the preparation of superabsorbent polymer.

Specifically, as the polymerization initiators, a thermal polymerization initiator or a photopolymerization initiator according to UV irradiation may be used according to polymerization methods. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

As the photopolymerization initiator, for example, one or more selected from the group consisting of benzoin ether, dialkyl acetophenone, hydroxyl alkylketone, phenyl glyoxylate, benzyl dimethyl ketal, acyl phosphine, and α-aminoketone may be used. As the specific example of the acyl phosphine, commercially used lucirin TPO, namely, 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, and are not limited to the above described examples.

And, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and, specific examples of the azo initiator may include 2,2-azobis (2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl)propane]dihydrochloride, 4,4-azobis-(4-cyanovalericacid), etc. More various thermal initiators are described in "Principle of Polymerization (Wiley, 1981)", Odian, page 203, and are not limited to the above described examples.

Here, the concentration of the polymer aqueous solution comprising polymer may be controlled such that the concentration of the polymer becomes about 20 to about 60 wt %, or about 40 to about 50 wt %, considering the easiness an economical feasibility of the process.

Next, sodium hydroxide (NaOH) is added to the polymer aqueous solution to prepare a neutralized spinning solution.

It is preferable to add the sodium hydroxide such that the neutralization degree of the spinning solution becomes about 40 to about 95 mol %, preferably about 50 to about 90 mol %, more preferably about 70 to about 80 mol %. As used herein, the neutralization degree is a value calculated by a Formula when measuring water soluble components.

If the neutralization degree is too low, the functional groups ionized in the polymer may be small, thus decreasing osmotic pressure, and if the neutralization degree is too high, although osmotic pressure is high, the number of functional groups capable of crosslinking may become small, and the crosslinked structure may not be sufficiently formed, and thus, it is preferable to have a neutralization degree in the above range.

In the conventional preparation method of superabsorbent polymer powder, the polymerization of a monomer composition neutralized with sodium hydroxide is progressed to form polymer, while in the preparation method of the present invention, polymerization is progressed first, and the neutralization degree of a polymer aqueous solution comprising polymer is controlled, and then, spinning is conducted to prepare superabsorbent polymer fiber. As such, by conducting neutralization of the polymer aqueous solution, a part of the polymer main chain may be ionized to draw water through osmosis by ions.

According to one embodiment of the present invention, the spinning solution may further comprise organic acid.

The organic acid may function as a catalyst that promotes a crosslinking reaction so as to effectively form a crosslinked structure even at lower drying temperature.

The organic acid that can be used is not specifically limited, but may include oxalic acid, acetic acid, lactic acid, citric acid, fumaric acid, tartaric acid, or maleic acid, etc. and preferably, oxalic acid may be used.

And, it may be used in the content of about 0.01 to about 5 parts by weight, or about 0.1 to about 2 parts by weight, based on 100 parts by weight of the polymer.

Next, the neutralized spinning solution is put in a spinnerette to conduct centrifugal spinning, and then, dried to prepare superabsorbent polymer fiber.

The centrifugal spinning is a method wherein polymer of a molten or solution state is put in a spinnerette having plural holes and rotated at high speed, and using the centrifugal force acted at this time, non-solidified polymer is elongated to make fine, and solidified fiber is stacked on a collector, and the fiber prepared by the method is obtained in the form of non-woven fabric. The centrifugal spinning has advantages in that the construction of equipment is simple, energy consumption is small, there is a small limitation in the usable polymers, and the process can be simplified because the fiber is prepared in the form of non-woven fabric through direct spinning on a substrate.

According to one embodiment of the present invention, the rotation speed of the centrifugal spinning may be about 3,000 rpm to about 15,000 rpm, but is not limited thereto. When centrifugally spinning at the above rotation speed, the spinning solution may be directly spun on a substrate, thus simplifying the process.

And, the size of the hole of the spinnerette may be about 100 to about 1,000 μm, or about 200 to about 800 μm, but is not limited thereto.

As explained above, the spinning solution is centrifugally spun, and then, drying is conducted immediately.

The drying may be conducted at a drying temperature of about 100 to about 250° C., or about 190 to about 250° C. for about 10 minutes to about 120 minutes.

Meanwhile, the drying temperature may be defined as the temperature of heating medium supplied for drying or the temperature of a drying reactor including heating medium and polymer in the drying process. If the drying temperature is less than about 100° C., a drying time may too lengthen, and the properties of the finally prepared superabsorbent polymer fiber may be deteriorated, and if the drying temperature is greater than about 250° C., only the surface of the fiber may be dried, and the properties of the finally prepared superabsorbent polymer fiber may be deteriorated. Preferably, the drying may be progressed at a temperature of about 100 to about 250° C., more preferably at about 160 to about 220° C.

And, the drying may be progressed for about 10 minutes to about 120 minutes, more preferably 20 minutes to 90 minutes, considering the process efficiency, etc., but the drying time is not limited thereto.

And, the drying method is not limited in terms of the construction as long as it can be commonly used as a drying process. Specifically, in the drying step, hot wind supply, infrared ray irradiation, ultrahigh frequency wave irradiation, or UV irradiation, etc., may be applied.

According to one embodiment of the present invention, the fiber is preferably non-woven fabric, but is not limited thereto.

The superabsorbent polymer fiber according to the present invention may be appropriately used for hygienic products or molded resin products, etc. Here, the molded resin product may comprise the polymer fiber of the above embodiment, or may consist only of such polymer fiber.

The use of such molded resin products is not specifically limited, and molded products used in various fields such as medical science, chemistry, chemical engineering, food or cosmetics, etc. may be included.

And, according to another embodiment of the present invention, superabsorbent polymer fiber prepared by the above preparation method is provided.

Since the superabsorbent polymer fiber has super absorbency to moisture under no pressure or pressurized environment, and simultaneously, exhibits flexibility and processibility, it can be modified into various shapes, and thus, can be applied more widely.

Hereinafter, the present invention will be explained in more detail through the examples. However, these examples are presented only as the illustrations of the invention, and the scope of the present invention is not limited thereby. The scope of the present invention is designated in the claims, and includes all the modifications within the meaning and scope equivalent to the description of the claims. And, "%" and "parts" indicating the contents in Examples and Comparative Examples below are based on mass, unless otherwise mentioned.

EXAMPLE

Preparation of Superabsorbent Polymer Fiber

Example 1

Polymerization was conducted to obtain a polymer aqueous solution by the following process. First, into a reactor, 120.8 g of water was introduced, the temperature was raised to 80° C., and the reactor was purged with nitrogen for 50 minutes, and then, 0.04 g of ammonium persulfate was introduced. Next, 99.2 g (1.38 mol) of acrylic acid, 0.8 g ($6.98*10^{-3}$ mol) of hydroxy ethyl acrylate as a crosslinking agent, 0.125 g of 2-mercaptoethanol as a chain transfer agent, and 0.1 g of ammonium persulfate as a polymerization initiator were mixed, and the mixture was reacted while being continuously introduced into the reactor for 4 hours. Thereafter, in order to remove unreacted monomers, 0.02 g of ammonium persulfate was introduced, and aging for 2 hours gave a polymer aqueous solution comprising 41.4 wt % of polyacrylic acid (Mw=447,000 g/mol).

To 5 g of the polymer aqueous solution, caustic soda (NaOH) was added to prepare a spinning solution with a neutralization degree adjusted to 80 mol %.

5 g of the spinning solution was introduced into a spinnerette with a hole size of 600 μm of centrifugal spinning machine (FibeRio, USA), and then, spun on a substrate made of cotton (50 gsm, 50 cm Φ) at a rotation speed per minute (rpm) of 11,000, and a sample was collected.

The collected sample was dried at 210° C. for 30 minutes using a convection oven to prepare superabsorbent polymer fiber in the form of non-woven fabric.

Example 2

Polymerization was conducted to obtain a polymer aqueous solution by the following process. First, into a reactor, 120.8 g of water was introduced, the temperature was raised to 80° C., and the reactor was purged with nitrogen for 50 minutes, and then, 0.04 g of ammonium persulfate was introduced. Next, 98.4 g (1.365 mol) of acrylic acid, 1.6 g ($1.38*10^{-2}$ mol) of hydroxy ethyl acrylate as a crosslinking agent, 0.125 g of 2-mercaptoethanol as a chain transfer agent, and 0.1 g of ammonium persulfate as a polymerization initiator were mixed, and the mixture was reacted while being continuously introduced into the reactor for 4 hours. Thereafter, in order to remove unreacted monomers, 0.02 g of ammonium persulfate was introduced, and aging for 2 hours gave a polymer aqueous solution comprising 41.9 wt % of polyacrylic acid (Mw=523,000 g/mol).

To 5 g of the polymer aqueous solution, caustic soda (NaOH) was added to prepare a spinning solution with a neutralization degree adjusted to 80 mol %.

5 g of the spinning solution was introduced into a spinnerette with a hole size of 600 μm of centrifugal spinning machine (FibeRio, USA), and then, spun on a substrate made of cotton (50 gsm, 50 cm Φ) at a rotation speed per minute (rpm) of 11,000, and a sample was collected.

The collected sample was dried at 210° C. for 30 minutes using a convection oven to prepare superabsorbent polymer fiber in the form of non-woven fabric.

Example 3

Polymerization was conducted to obtain a polymer aqueous solution by the following process. First, into a reactor, 120.8 g of water was introduced, the temperature was raised to 80° C., and the reactor was purged with nitrogen for 50 minutes, and then, 0.04 g of ammonium persulfate was introduced. Next, 99.1 g (1.375 mol) of acrylic acid, 0.9 g ($6.915*10^{-3}$ mol) of hydroxy ethyl methacrylate as a crosslinking agent, 0.125 g of 2-mercaptoethanol as a chain transfer agent, and 0.1 g of ammonium persulfate as a polymerization initiator were mixed, and the mixture was reacted while being continuously introduced into the reactor for 4 hours. Thereafter, in order to remove unreacted monomers, 0.02 g of ammonium persulfate was introduced, and aging for 2 hours gave a polymer aqueous solution comprising 41.6 wt % of polyacrylic acid (Mw=480,000 g/mol).

To 5 g of the polymer aqueous solution, caustic soda (NaOH) was added to prepare a spinning solution with a neutralization degree adjusted to 80 mol %.

5 g of the spinning solution was introduced into a spinnerette with a hole size of 600 μm of centrifugal spinning machine (FibeRio, USA), and then, spun on a substrate made of cotton (50 gsm, 50 cm Φ) at a rotation speed per minute (rpm) of 11,000, and a sample was collected.

The collected sample was dried at 210° C. for 30 minutes using a convection oven to prepare superabsorbent polymer fiber in the form of non-woven fabric.

Example 4

Polymerization was conducted to obtain a polymer aqueous solution by the following process. First, into a reactor, 120.8 g of water was introduced, the temperature was raised to 80° C., and the reactor was purged with nitrogen for 50 minutes, and then, 0.04 g of ammonium persulfate was introduced. Next, 98.2 g (1.363 mol) of acrylic acid, 1.8 g ($1.38*10^{-2}$ mol) of hydroxy ethyl methacrylate as a crosslinking agent, 0.125 g of 2-mercaptoethanol as a chain transfer agent, and 0.1 g of ammonium persulfate as a polymerization initiator were mixed, and the mixture was reacted while being continuously introduced into the reactor for 4 hours. Thereafter, in order to remove unreacted monomers, 0.02 g of ammonium persulfate was introduced, and aging for 2 hours gave a polymer aqueous solution comprising 41.3 wt % of polyacrylic acid (Mw=539,000 g/mol).

To 5 g of the polymer aqueous solution, caustic soda (NaOH) was added to prepare a spinning solution with a neutralization degree adjusted to 80 mol %.

5 g of the spinning solution was introduced into a spinnerette with a hole size of 600 μm of centrifugal spinning machine (FibeRio, USA), and then, spun on a substrate made of cotton (50 gsm, 50 cm Φ) at a rotation speed per minute (rpm) of 11,000, and a sample was collected.

The collected sample was dried at 210° C. for 30 minutes using a convection oven to prepare superabsorbent polymer fiber in the form of non-woven fabric.

Example 5

Polymerization was conducted to obtain a polymer aqueous solution by the following process. First, into a reactor, 120.8 g of water was introduced, the temperature was raised to 80° C., and the reactor was purged with nitrogen for 50 minutes, and then, 0.04 g of ammonium persulfate was introduced. Next, 98.4 g (1.365 mol) of acrylic acid, 1.6 g (1.38*10$^{-2}$ mol) of hydroxy ethyl acrylate as a crosslinking agent, 0.125 g of 2-mercaptoethanol as a chain transfer agent, and 0.1 g of ammonium persulfate as a polymerization initiator were mixed, and the mixture was reacted while being continuously introduced into the reactor for 4 hours. Thereafter, in order to remove unreacted monomers, 0.02 g of ammonium persulfate was introduced, and aging for 2 hours gave a polymer aqueous solution comprising 41.9 wt % of polyacrylic acid (Mw=523,000 g/mol).

To 5 g of the polymer aqueous solution, caustic soda (NaOH) was added to adjust the neutralization degree to 80 mol %, and 0.0336 g (3.732*10$^{-4}$ mol) of oxalic acid was added to prepare a spinning solution.

5 g of the spinning solution was introduced into a spinnerette with a hole size of 600 μm of centrifugal spinning machine (FibeRio, USA), and then, spun on a substrate made of cotton (50 gsm, 50 cm Φ) at a rotation speed per minute (rpm) of 11,000, and a sample was collected.

The collected sample was dried at 200° C. for 30 minutes using a convection oven to prepare superabsorbent polymer fiber in the form of non-woven fabric.

Example 6

Polymerization was conducted to obtain a polymer aqueous solution by the following process. First, into a reactor, 120.8 g of water was introduced, the temperature was raised to 80° C., and the reactor was purged with nitrogen for 50 minutes, and then, 0.04 g of ammonium persulfate was introduced. Next, 98.4 g (1.365 mol) of acrylic acid, 1.6 g (1.38*10$^{-2}$ mol) of hydroxy ethyl acrylate as a crosslinking agent, 0.125 g of 2-mercaptoethanol as a chain transfer agent, and 0.1 g of ammonium persulfate as a polymerization initiator were mixed, and the mixture was reacted while being continuously introduced into the reactor for 4 hours. Thereafter, in order to remove unreacted monomers, 0.02 g of ammonium persulfate was introduced, and aging for 2 hours gave a polymer aqueous solution comprising 41.9 wt % of polyacrylic acid (Mw=523,000 g/mol).

To 5 g of the polymer aqueous solution, caustic soda (NaOH) was added to adjust a neutralization degree to 80 mol %, and 0.0336 g (3.732*10$^{-4}$ mol) of oxalic acid was added to prepare a spinning solution.

5 g of the spinning solution was introduced into a spinnerette with a hole size of 600 μm of centrifugal spinning machine (FibeRio, USA), and then, spun on a substrate made of cotton (50 gsm, 50 cm Φ) at a rotation speed per minute (rpm) of 11,000, and a sample was collected.

The collected sample was dried at 190° C. for 30 minutes using a convection oven to prepare superabsorbent polymer fiber in the form of non-woven fabric.

Experimental Example

Property Evaluation of Superabsorbent Polymer Fiber

For the superabsorbent polymer fiber prepared in Examples 1 to 6, the properties were measured as follows, and the results are shown in Table 1.

(1) Centrifugal Retention Capacity (CRC)

The centrifugal retention capacity was measured according to EDANA method WSP 241.3. Among the prepared superabsorbent polymer fiber, 0.2 g of the sample was put in a tea bag and soaked in a 0.9% saline (NaCl) solution for 30 minutes.

After draining at the centrifugal force of 250 G for 3 minutes, the amount of the saline solution absorbed was measured.

(2) Absorption Under Load (AUL)

The absorption under load was measured according to EDANA method WSP 242.3. Among the prepared superabsorbent polymer fiber, 0.16 g of the sample was put in a cylinder prescribed in EDANA, and a pressure of 0.3 pis was applied with a piston and a weight. And then, the amount of the 0.9% saline solution absorbed was measured.

TABLE 1

|  | CRC (g/g) | AUL (g/g) |
| --- | --- | --- |
| Example 1 | 20.8 | 20.3 |
| Example 2 | 20.1 | 21.3 |
| Example 3 | 22.7 | 15.7 |
| Example 4 | 19.1 | 19.1 |
| Example 5 | 19.6 | 19.4 |
| Example 6 | 34.8 | 10.6 |

(3) Scanning Electron Microscope (SEM) Analysis

Figure 2:
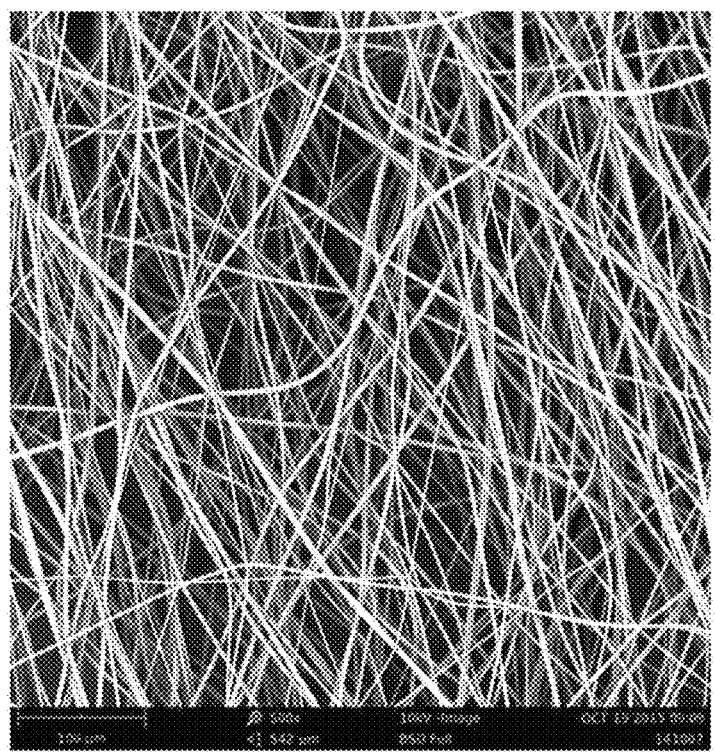
FIG. 2 is the Scanning Electron Microscope (SEM) photograph the superabsorbent polymer fiber according to example of the present invention.

The photograph of the superabsorbent polymer fiber prepared in Example 1 of the present invention was shown in FIG. 1, and the Scanning electron microscope (SEM) photograph of the superabsorbent polymer fiber with a magnification of 500 times was shown in FIG. 2.

Referring to FIGS. 1 and 2, it was confirmed that fiber with a yarn width of about 5 μm was successfully prepared by the preparation method of the present invention, and that it was obtained in the form of non-woven fabric.

What is claimed is:

1. A method for preparing superabsorbent polymer fiber comprising the steps of:
   polymerizing water-soluble ethylenically unsaturated monomers and a crosslinking agent to prepare a polymer aqueous solution, wherein the polymer aqueous solution comprising a polymer, wherein the polymer being copolymerized from the water-soluble ethylenically unsaturated monomers and the crosslinking agent, wherein a molar ratio of the water-soluble ethylenically unsaturated monomers and crosslinking agent is 97:3 to 99.9:0.1;
   adding sodium hydroxide to the polymer aqueous solution to prepare a neutralized spinning solution; and
   centrifugally spinning the neutralized spinning solution onto a substrate; and drying the substrate to prepare the superabsorbent polymer fiber, wherein the drying is conducted a temperature of 100 to 250° C. for 10 minutes to 120 minutes.

2. The method for preparing superabsorbent polymer fiber according to claim 1, wherein the water-soluble ethylenically unsaturated monomers are one or more selected from the group consisting of anionic monomers, non-ionic hydrophilic group containing monomers, and amino group containing unsaturated monomers.

3. The method for preparing superabsorbent polymer fiber according to claim 1, wherein the crosslinking agent is one or more selected from the group consisting of hydroxyl alkyl (meth)acrylate-based compounds, polyhydric alcohol compounds; (meth)acrylate-based compounds, epoxy compounds, polyamine compounds, haloepoxy compounds, condensation products of haloepoxy compounds, oxazoline compounds, mono-, di- or polyoxazolidinone compounds, cyclic urea compounds, multivalent metal salts, and alkylene carbonate compounds.

4. The method for preparing superabsorbent polymer fiber according to claim 1, wherein organic acid is further added to the spinning solution.

5. The method for preparing superabsorbent polymer fiber according to claim 4, wherein the organic acid is one or more selected from the group consisting of oxalic acid, acetic acid, lactic acid, citric acid, fumaric acid, tartaric acid, and maleic acid.

6. The method for preparing superabsorbent polymer fiber according to claim 1, wherein the polymer of the water-soluble ethylenically unsaturated monomers and crosslinking agent is polyacrylic acid.

7. The method for preparing superabsorbent polymer fiber according to claim 1, wherein the neutralization degree of the spinning solution is 40 to 95 mol %.

8. The method for preparing superabsorbent polymer fiber according to claim 1, wherein the fiber is non-woven fabric.

9. The method for preparing superabsorbent polymer fiber according to claim 1, wherein a rotation speed during the centrifugal spinning is 3,000 to 15,000 rpm.

10. Hygienic products including superabsorbent polymer fibers prepared by the method according to claim 1.

11. A superabsorbent polymer fiber obtained by the preparation method of claim 1.

12. The method for preparing superabsorbent polymer fiber according to claim 2, wherein the anionic monomers are selected from the group consisting of acrylic acid, polyacrylic acid, methacrylic acid, maleic anhydride, fumaric acid, crotonic acid, itaconic acid, 2-acryloylethane sulfonic acid, 2-methacryloylethane sulfonic acid, 2-(meth) acryloylpropane sulfonic acid or 2-(meth)acrylamide-2-methyl propane sulfonic acid, and salts thereof.

13. The method for preparing superabsorbent polymer fiber according to claim 2, wherein the non-ionic hydrophilic group containing monomers are selected from the group consisting of (meth)acrylamide, N-substituted (meth)acrylate, 2-hydroxyethyl (meth)acrylate, methylacrylate, methoxy polyethylene glycol (meth)acrylate, and polyethylene glycol (meth)acrylate.

14. The method for preparing superabsorbent polymer fiber according to claim 2, wherein the amino group containing unsaturated monomers are selected from the group consisting of (N,N)-dimethylaminoethyl (meth)acrylate, (N,N)-dimethylaminopropyl (meth)acrylamide, and quarternarized products thereof.

* * * * *